US005782858A

United States Patent [19]

Cheng

[11] Patent Number: 5,782,858

[45] Date of Patent: Jul. 21, 1998

[54] APPARATUS FOR TREATING THE EYES PHYSICALLY

[76] Inventor: Chih Shun Cheng, 229, Chu Jen Street, Pai Ho Cheng Tainan Hsien, Taiwan

[21] Appl. No.: 858,733

[22] Filed: May 19, 1997

[51] Int. Cl.$^{6}$ .......... A61H 7/00

[52] U.S. Cl. .......... 606/204; 606/189; 600/9

[58] Field of Search .......... 606/189, 204; 600/9, 13, 14, 15

[56] References Cited

U.S. PATENT DOCUMENTS 5,099,829 3/1992 Wu .......... 601/46

5,134,991 8/1992 Hustead .......... 606/204

5,560,746 10/1996 Willow .......... 601/135

*Primary Examiner*—Michael Buiz

*Assistant Examiner*—David O. Reip

*Attorney, Agent, or Firm*—Pro-Techtor International

[57] ABSTRACT

A medical apparatus which includes a first magnetic energy device with a magnetically conductive, rounded, pointed front end for acupuncturing acupuncture points of the fingers and around the eyes by means of a magnetic resonance, and a second magnetic energy device with a magnetically conductive concave front end for stimulating the orbicularis oculi muscle by means of a magnetic resonance.

2 Claims, 8 Drawing Sheets

10

13

11

131

10
11
13
131
C
B
A

APPARATUS FOR TREATING THE EYES PHYSICALLY

BACKGROUND OF THE INVENTION

The present invention relates to apparatus for treating the eyes physically, and more particularly to such a medical apparatus which comprises a first magnetic energy device and a second magnetic energy device for acupuncturing acupuncture points of the fingers and around the eyes and stimulating the orbicularis oculi muscle by means of a magnetic resonance.

When one's visual organ cannot function well, it must be medically treated. If a medical treatment cannot correct one's power of vision, a visual correction device for example a pair of glasses may have to be used. It is known that various conditions may cause the eyes unable to function well. These conditions include improper writing posture, malnutrition (lacking in protein and calcium), long exposure of the eyes to excessively high or low intensity of light, narrow field of vision, burning the mid-night oil, long exposure of the eyes to radiation, certain diseases such as hepatitis, diabetes, high eyeball tension, etc. In order not to exhaust the strength of the eyes, one must close the eyes and take a rest after a certain length of time in reading books or watching TV. There are know various devices designed for massaging the muscles around the eyes. However, these devices can only relax the muscles around the eyes, they are unable to reduce the tension of the eyeball.

SUMMARY OF THE INVENTION

It is the main object of the present invention to provide a handy apparatus which is practical for releasing the tension of the eyeball. It is another object of the present invention to provide an apparatus for treating the eye physically which acupunctures acupuncture points of the fingers and around the eyes and stimulates the orbicularis oculi muscle by means of a magnetic resonance. According to the preferred embodiment of the present invention, the apparatus comprises a first magnetic energy device with a magnetically conductive, rounded, pointed front end for acupuncturing acupuncture points of the fingers and around the eyes by means of a magnetic resonance, and a second magnetic energy device with a magnetically conductive concave front end for stimulating the orbicularis oculi muscle by means of a magnetic resonance.

DETAILED DESCRIPTION OF THE PREFERRED EMBODIMENT

Figure 1:
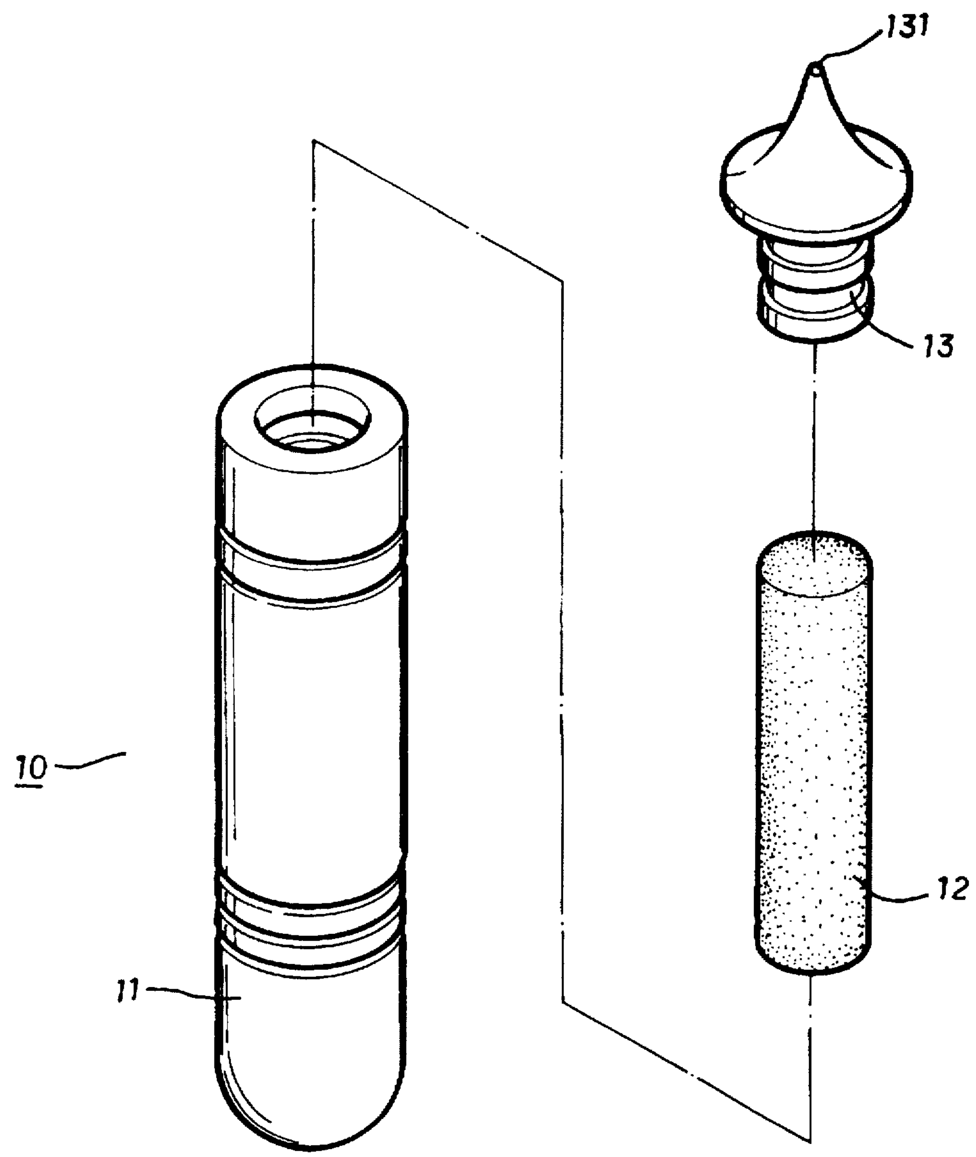
FIG. 1 is an exploded view of a first magnetic energy device according to the present invention.
Figure 2:
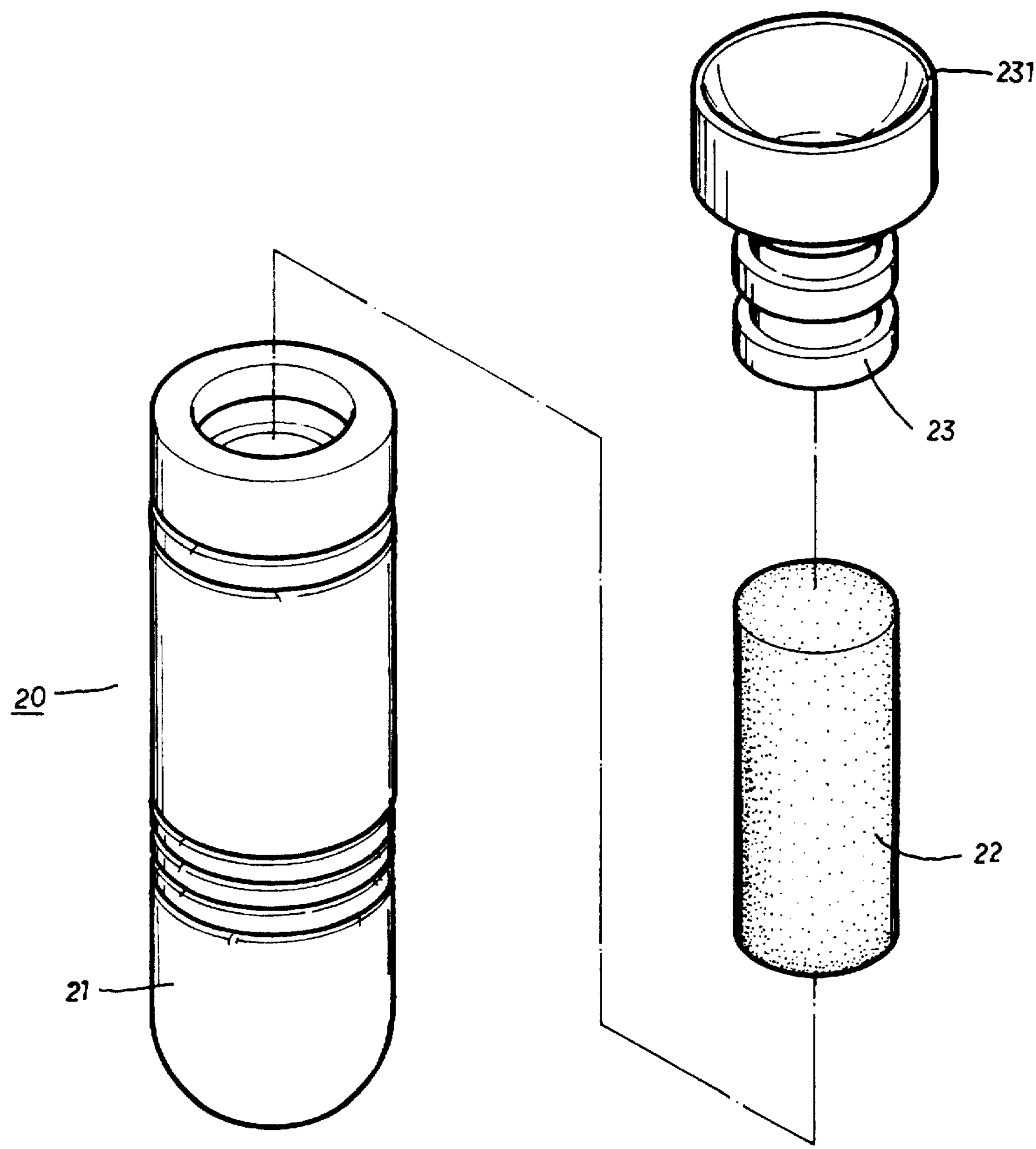
FIG. 2 is an exploded view of a second magnetic energy device according to the present invention.
Figure 6:
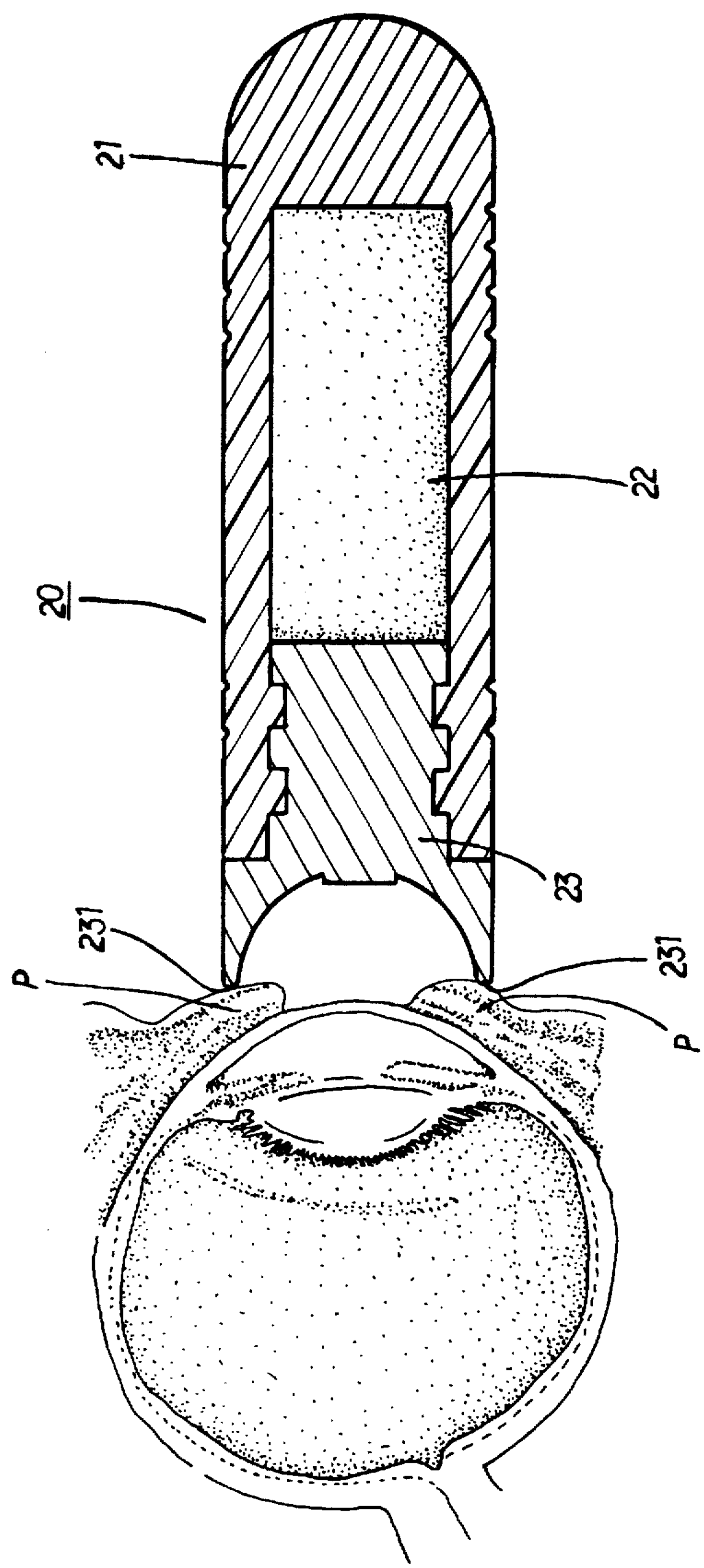
FIG. 6 is a sectional view showing the second magnetic energy device attached to the orbicularis oculi muscle of the eye according to the present invention.
Figure 11:
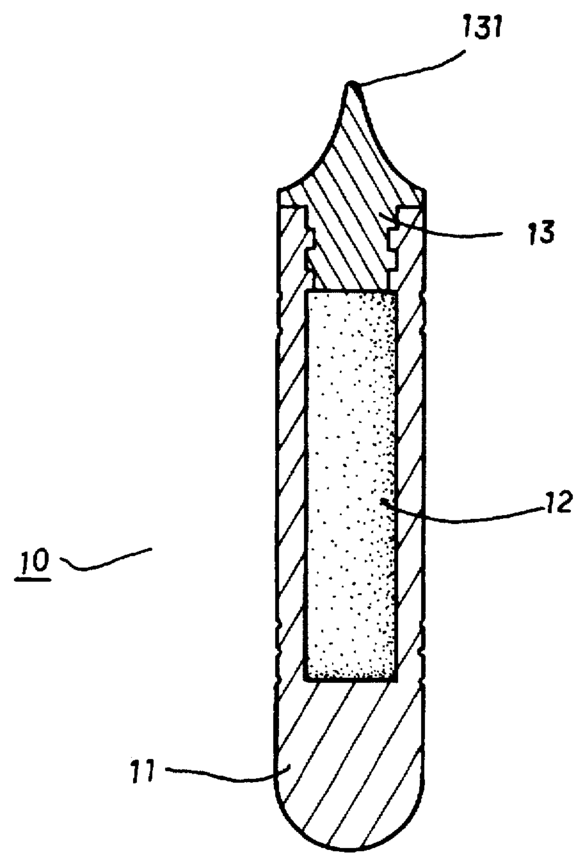
FIG. 11 is a sectional view of the first magnetic energy device according to the present invention.

Referring to FIGS. 1 and 2, the present invention comprises a first magnetic energy device 10, and a second magnetic energy device 20. The first magnetic energy device 10 comprises a cylindrical casing 11, an elongated permanent magnet 12, and a contact cap 13 fastened to the top open end of the cylindrical casing 11 by a screw joint (see FIG. 11). The contact cap 13 of the first magnetic energy device 10 has a conical front end terminating in a rounded contact tip 131. The second magnetic energy device 20 comprises a cylindrical casing 21, an elongated permanent magnet 22, and a contact cap 23 fastened to the top open end of the cylindrical casing 21 by a screw joint (see FIG. 6) The contact cap 23 of the second magnetic energy device 20 has a concave front contact surface 231. The cylindrical casing 11 of the first magnetic energy device 10 as well as the cylindrical casing 21 of the second magnetic energy device 20 are shaped like a test tube having a bottom close end and a top open end, and made from magnetically insulative material. The contact caps 13;23 of the first and second magnetic energy devices 10;20 are made from magnetically conductive metal. The permanent magnets 12;22 produce a respective magnetic field having an intensity of about 2000 gausses to 4000 gausses.

Figure 3:
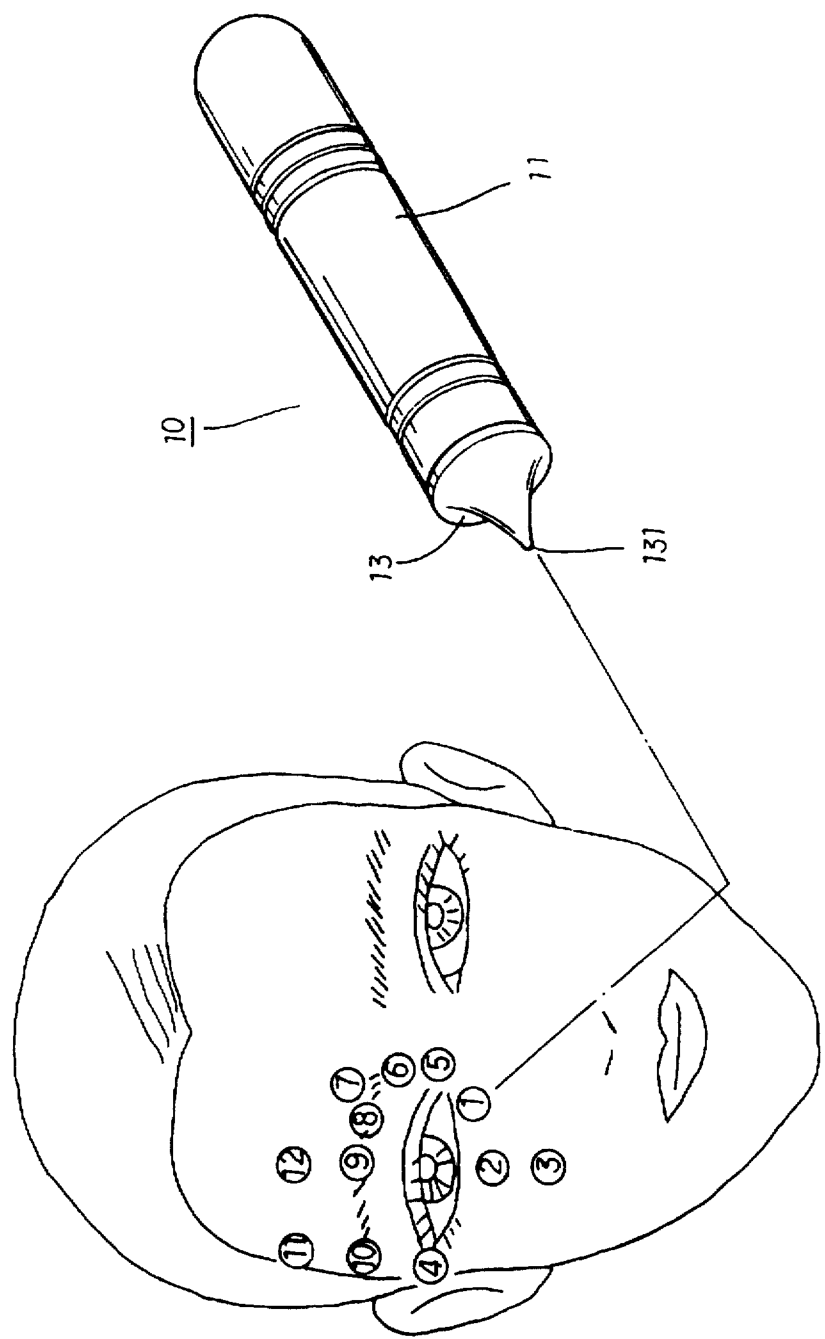
FIG. 3 shows the 12 acupuncture points around the eye to which the first magnetic energy device is to be applied.
Figure 4:
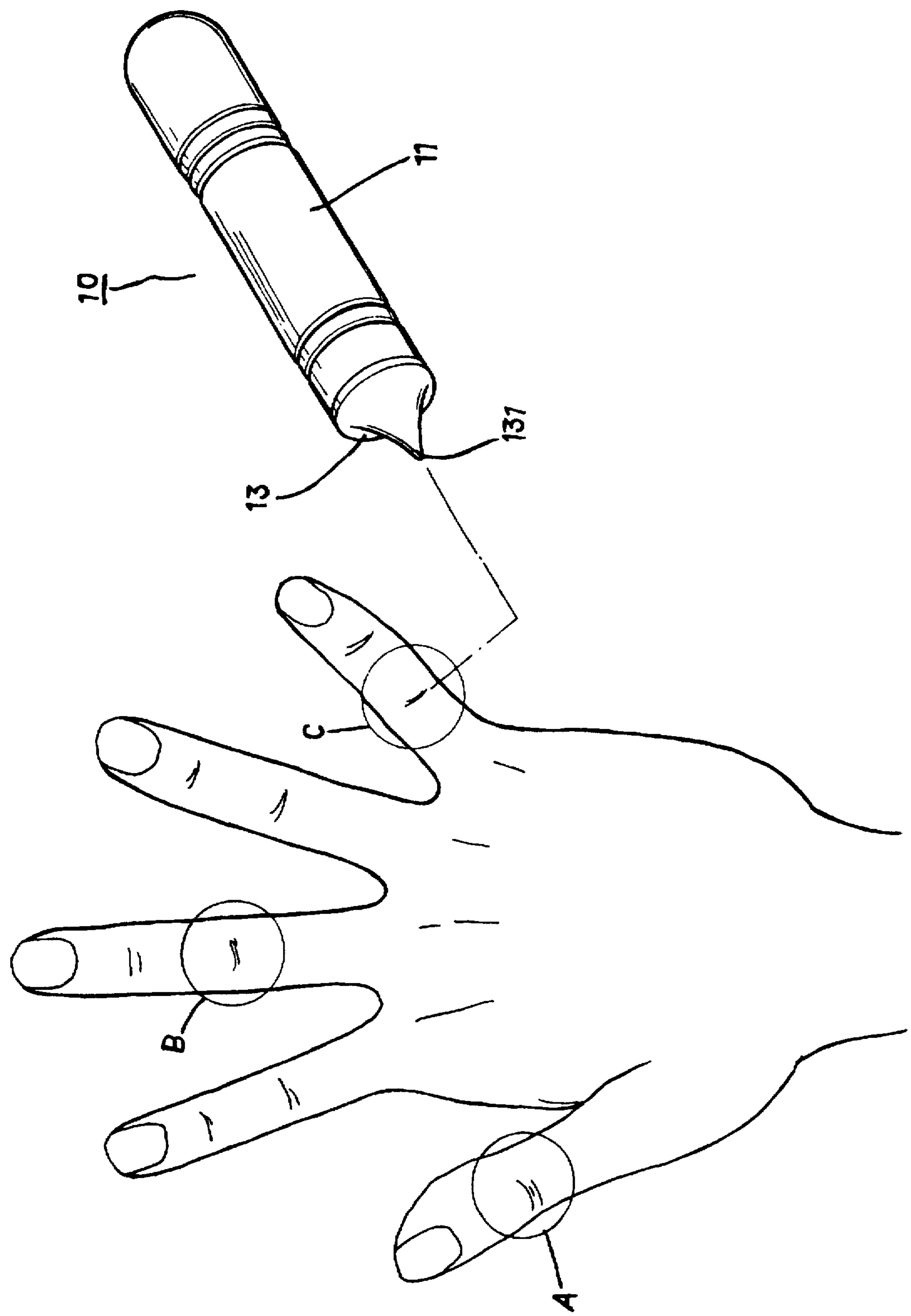
FIG. 4 shows three acupuncture points of the fingers to which the first magnetic energy device is to be applied.
Figure 5:
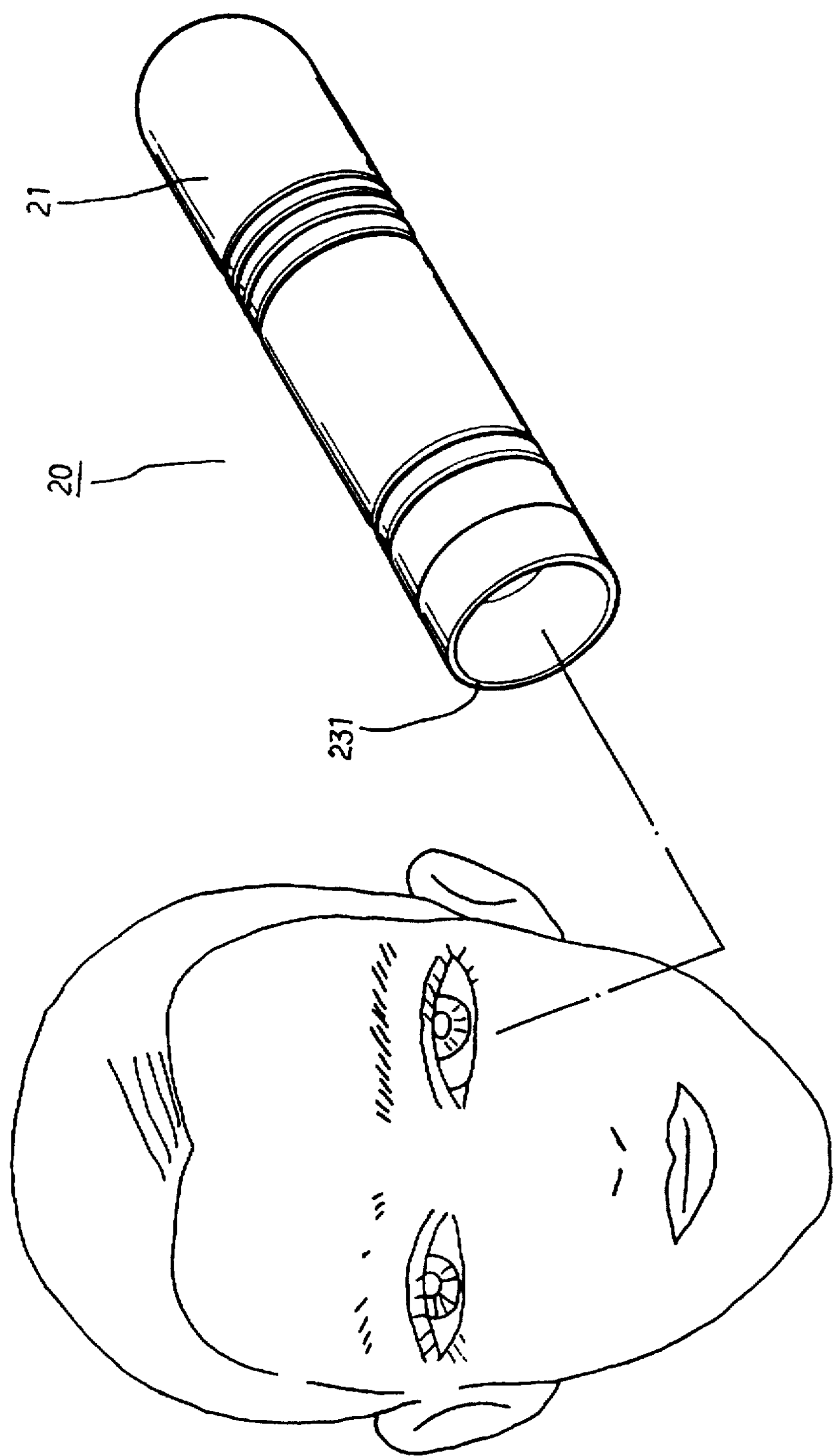
FIG. 5 shows the application area around the eye to which the second magnetic energy device is to be applied.

Referring to Figures from 3 to 6, the first magnetic energy device 10 is adapted to acupuncture twelve acupuncture points around the eye, namely, Jingming, Chengqi, Sibai, Tongziliao, Tianying I, Tianying II, Zanzhu, Ahshi, Yuyao, Sizhukon, Taiyang and Yangbai (see FIG. 3), and three acupuncture points at the fingers, namely, Takongu A, Takongu B, and Shiakongu (see FIG. 4) by attaching the rounded contact tip 131 of the contact cap 13 to each acupuncture point for about 10 to 20 minutes; the second magnetic energy device 20 is adapted to stimulate the orbicularis oculi muscle P of the eye by attaching the concave contact surface 231 of the contact cap 23 to the orbicularis oculi muscle P for about 10 to 20 minutes, so as to adjust the tension of the eyeball. When the magnetic cap 13 or 23 is attached to the body, the magnetic field of the magnetic energy device 10 or 20 and the magnetic field of the body produce a resonant effect which stimulates the circulation of blood and relaxes the muscle.

As it is known that the intensity of the magnetic field of the atmosphere is about 0.5 gauss, and the intensity of the magnetic field of the body is the product of the intensity of the magnetic field of the atmosphere and the volume of the body, i.e., about 4000 gausses for an adult or 2000 gausses for a child. Therefore, the intensity of the magnetic field of the permanent magnets 12;22 is set at about 2000 gausses to 4000 gausses so that it can produce a resonant effect with the intensity of the magnetic field of the body.

Figure 7:
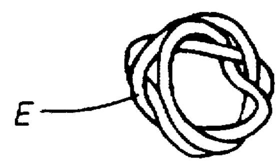
FIG. 7 shows a twisted new elastic band thrown toward the table top.
Figure 8:
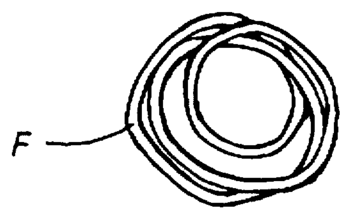
FIG. 8 shows an used elastic band twisted and thrown toward the table top.
Figure 9:
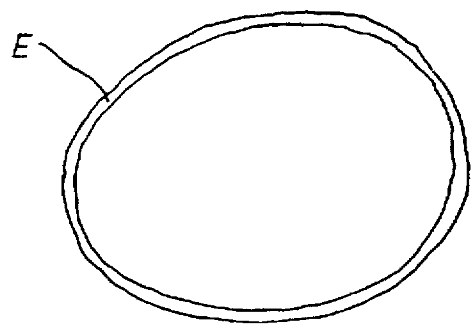
FIG. 9 shows the elastic band of FIG. 7 returned to its former shape.
Figure 10:
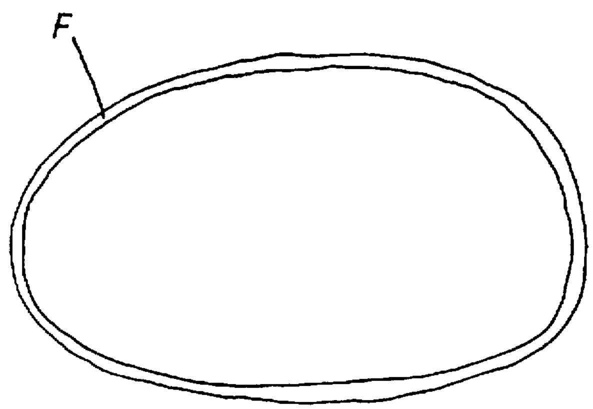
FIG. 10 shows the elastic band of FIG. 8 returned to its former shape.

Referring to Figures from 7 to 10, when a new elastic band E is twisted and then thrown to the table top (see FIG. 7), it immediately returns to its former shape by means of its springy material property (see FIG. 9); when an used elastic band F which has less springy power is twisted and then thrown to the table top (see FIG. 8), it returns to its former shape (see FIG. 10) only after several throws against the table top. Each time the elastic band F is thrown against the table top, it receives an impact force, and the impact force forces the elastic band F to change its shape. Similarly, the application of the present invention causes a resonant effect which stimulates the circulation of blood and the muscle, causing the muscle to work better.

While only one embodiment of the present invention has been shown and described, it will be understood that various modifications and changes could be made thereunto without departing from the spirit and scope of the invention disclosed.

What the invention claimed is:

1. A medical apparatus comprising a first magnetic energy device and a second magnetic energy device for acupuncturing acupuncture points of the fingers and around the eyes and stimulating the orbicularis oculi muscle by means of a magnetic resonance, said first magnetic energy device and said second magnetic energy device comprising each a cylindrical casing made from magnetically insulative material having a bottom close and a top open end, an elongated permanent magnet mounted inside said cylindrical casing, and a contact cap made from magnetically conductive material and fastened to the top open end of said cylindrical casing by a screw joint, the contact cap of said first magnetic energy device having a conical front end terminating in a rounded contact tip, the contact cap of said second magnetic energy device having a concave front contact surface.

2. The medical apparatus of claim 1, wherein the intensity of the magnetic field of said permanent magnet is about 2000 gausses to 4000 gausses.

* * * * *